(12) United States Patent
Zemlok et al.

(10) Patent No.: US 7,954,687 B2
(45) Date of Patent: Jun. 7, 2011

(54) COATED SURGICAL STAPLES AND AN ILLUMINATED STAPLE CARTRIDGE FOR A SURGICAL STAPLING INSTRUMENT

(75) Inventors: Michael Zemlok, Prospect, CT (US); Adam J. Ross, East Hampton, CT (US); Peter Hathaway, Lebanon, CT (US)

(73) Assignee: Tyco Healthcare Group LP, North Haven, CT (US)

( * ) Notice: Subject to any disclaimer, the term of this patent is extended or adjusted under 35 U.S.C. 154(b) by 230 days.

(21) Appl. No.: 12/262,243

(22) Filed: Oct. 31, 2008

(65) Prior Publication Data

US 2009/0114701 A1     May 7, 2009

Related U.S. Application Data

(60) Provisional application No. 60/985,661, filed on Nov. 6, 2007.

(51) Int. Cl.
*A61B 17/068* (2006.01)
(52) U.S. Cl. ............... 227/176.1; 227/19; 227/175.1; 411/444; 411/457; 411/920; 606/219
(58) Field of Classification Search ............ 227/19, 227/176.1, 175.1, 180.1, 178.1; 606/139, 606/219; 411/457, 473, 444, 920
See application file for complete search history.

(56) References Cited

U.S. PATENT DOCUMENTS

| | | | | |
|---|---|---|---|---|
| 4,645,111 A * | 2/1987 | Larrabee et al. | ........... | 227/19 |
| 4,813,586 A * | 3/1989 | Seifert | ........... | 227/19 |
| 4,925,082 A * | 5/1990 | Kim | ........... | 227/120 |
| 5,395,030 A | 3/1995 | Kuramoto et al. | | |
| 5,501,387 A * | 3/1996 | Yoshie | ........... | 227/120 |
| 5,662,683 A * | 9/1997 | Kay | ........... | 606/232 |
| 5,868,760 A * | 2/1999 | McGuckin, Jr. | ........... | 606/139 |
| 6,206,897 B1 * | 3/2001 | Jamiolkowski et al. | ....... | 606/157 |
| 6,264,086 B1 * | 7/2001 | McGuckin, Jr. | ........... | 227/180.1 |
| 7,237,708 B1 | 7/2007 | Guy et al. | | |
| 7,464,847 B2 | 12/2008 | Viola et al. | | |
| 2002/0013605 A1 | 1/2002 | Bolduc et al. | | |
| 2005/0131390 A1 | 6/2005 | Heinrich et al. | | |
| 2006/0235469 A1 | 10/2006 | Viola | | |

FOREIGN PATENT DOCUMENTS

| | | |
|---|---|---|
| DE | 3213304 | 10/1983 |
| EP | 0714633 | 6/1996 |
| EP | 1362554 | 11/2003 |
| EP | 1616526 | 1/2006 |

(Continued)

OTHER PUBLICATIONS

European Search Report for EP 08253611.1-2310 date of completion is Mar. 12, 2009 (6 pages).

(Continued)

*Primary Examiner* — Scott A. Smith (57) ABSTRACT

A coated surgical fastener is provided for an easy visualization within tissue. The coated surgical fastener includes a core and a relatively non-reflective coating applied about the core. There is also disclosed an illuminated staple cartridge for use with a surgical stapling device having a light source. The illuminated staple cartridge includes a transparent insert and a relatively nontransparent U-shaped outer channel at least partially surrounding the transparent insert. Windows formed in sides of the U-shaped outer channel allow defined amounts of light to project from the sides of the illuminated staple cartridge.

13 Claims, 5 Drawing Sheets

FOREIGN PATENT DOCUMENTS

| | | |
|---|---|---|
| EP | 1754445 | 2/2007 |
| EP | 1772110 | 4/2007 |
| WO | WO96/18344 | 6/1996 |
| WO | WO97/07744 | 3/1997 |
| WO | WO02/19918 | 3/2002 |
| WO | WO03/075979 | 9/2003 |
| WO | WO2007/005621 | 1/2007 |

OTHER PUBLICATIONS

European Search Report for EP 08253611.1-2310 date of completion is Aug. 27, 2009 (6 pages).

* cited by examiner

COATED SURGICAL STAPLES AND AN ILLUMINATED STAPLE CARTRIDGE FOR A SURGICAL STAPLING INSTRUMENT

CROSS REFERENCE TO RELATED APPLICATIONS

This application claims benefit of U.S. Provisional Application Ser. No. 60/985,661 filed Nov. 6, 2007, the disclosures of which are hereby incorporated by reference herein, in their entirety.

BACKGROUND

1. Technical Field

The present disclosure relates to surgical staples for use in a surgical stapling instrument. More particularly, the present disclosure relates to surgical staples coated to enhance visibility of placement in tissue. The present disclosure further relates to a staple cartridge having internal illumination to enhance visibility of the cartridge's position in tissue and positioning of the internal components of the staple cartridge.

2. Background of Related Art

During certain surgical procedures various surgical stapling devices are used to apply one or more rows of staples to tissue and, in some cases, cut the tissue between the rows of staples. The visibility of the distal end of the stapling device used within the body of a patient is important to insure proper placement of the stapling device about tissue. The ability to visually monitor the distal end of the surgical stapling device is also useful to determine how much tissue has actually been stapled and/or how much of the tissue has actually been cut by the surgical stapling device.

The ability to visualize the distal end of the surgical stapling device is more difficult when the surgical stapling device is used endoscopically or laparoscopically. In these situations, the surgical stapling device is inserted into the body through a port in the body. The surgical operation is performed under visualization through an endoscope or laparoscope having a limited field of view. This may make it difficult to verify that the surgical stapling device has functioned properly and to evaluate the integrity of the staple line formed by the surgical stapling device.

The ability to evaluate the integrity of the staple line may be hindered by the use of conventional staples formed of stainless steel and/or titanium as these materials tend to reflect light back towards the lens in the endoscope or laparoscope obscuring a clear view of the staple line.

Thus, there is a need for a surgical stapling device having a distal end which can be more visible within the patient's body during use. There is also a need for a surgical fastener capable of being clearly visualized within the body without reflecting significant amounts of light back towards the viewing device.

SUMMARY

A surgical fastener is formed as a conventional U-shaped surgical staple having a backspan and a pair of legs extending distally from the backspan. Each of the legs terminates in a tissue penetrating tip. The surgical staple is coated with a material configured to enhance the visibility of the surgical staple within tissue while at the same time reducing the reflectivity of the surgical staple. In a specific embodiment, the tissue penetrating tips of the surgical staple are not coated so as to avoid blunting of the sharp tips.

In an alternative embodiment, the surgical fastener is formed as a helical coil fastener having a sharp distal tissue penetrating tip in a compressed proximal coil facilitating insertion in tissue. The disclosed helical coil fastener is coated to enhance visibility while reducing reflectivity.

There is also disclosed a staple cartridge for use with a surgical stapling device having a light source. The staple cartridge generally includes a U-shaped outer channel member and a transparent insert positioned within the U-shaped outer channel member. The transparent insert includes a body portion having a tapered leading edge and an upwardly facing surface for emitting light. In a particular embodiment, the U-shaped outer channel is formed with a series of longitudinally extending windows allowing light transmitted through side surfaces of the transparent insert to pass there through. In use, the relative positioning of staple drivers and a knife blade, associated with a surgical stapling device, attenuate the amount of light passing through the transparent insert and out through the windows in the U-shaped outer channel. The sled or pushers will block any light for distal light windows until it progresses past, thus indicating staple line positional status.

There is also disclosed a surgical stapling device having a staple cartridge to facilitate visual positioning of the distal end of the surgical stapling device within tissue. The staple cartridge is positioned on a distal end of the surgical stapling device such that a light source associated with the surgical stapling device is in position to transmit light to the transparent insert associated with the staple cartridge.

DESCRIPTION OF THE DRAWINGS

Various embodiments of the presently disclosed surgical staples and surgical instrument incorporating an illuminated staple cartridge are disclosed herein with reference to the drawings, wherein.

DETAILED DESCRIPTION OF EMBODIMENTS

Embodiments of the presently disclosed surgical fasteners and surgical stapling device will now be described in detail with reference to the drawings wherein like numerals designate identical or corresponding elements in each of the several views. As is common in the art, the term 'proximal" refers to that part or component closer to the user or operator, i.e. surgeon or physician, while the term "distal" refers to that part or component further away from the user.

Figure 1:
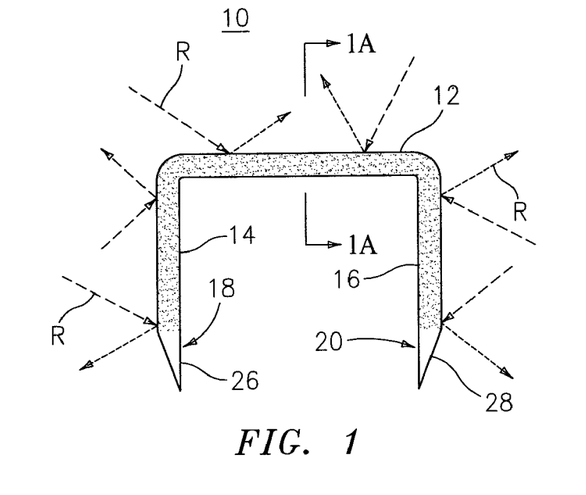
FIG. 1 is a side view of a coated surgical staple.

Referring to FIG. 1, there is disclosed a surgical fastener or surgical staple 10 which includes a coating, coloring or other material to assist in viewing the staple within the body of a patient and to assist in viewing the proper formation of staple 10 into the characteristic "B" fully formed shape. Staple 10 generally includes a backspan 12 having first and second legs 14 and 16, respectively, extending distally from backspan 12. First leg 14 terminates in a tissue penetrating tip 18 and second leg 16 terminates in a similar tissue penetrating tip 20.

Figure 1A:
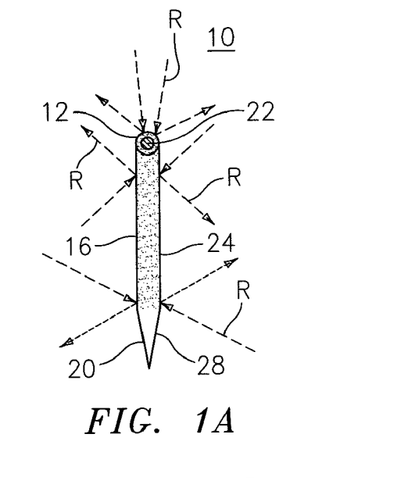
FIG. 1A is an end view, partially shown in section, of the coated surgical staple of FIG. 1.

Referring to FIGS. 1 and 1A, staple 10 includes a core 22 having an active coating 24 applied to core 22. Core 22 can be formed of a metallic substance such as, for example, stainless steel, titanium, or other deformable/malleable material etc. Active coating 24 may include of materials having molecular fluorescence, molecular phosphorescence, chemiluminescence, etc. which emit visible rays "R" enabling staple 10 to be easily visualized within the body of a patient. By coating core 22 with one or more of these active coatings 24, staple 10 can be visualized within the body of a patient without reliance on substantially reflected light. For example, some of the above coatings may be activated by ultraviolet light such that they fluorescence or "glow-in-the-dark". Alternatively, other of the above coatings emit their own sources of light to facilitate visualization of the staple or may emit no visible light such that the staple can be viewed due to substantial contrast against the underlying tissue.

In the formation of staple 10, the above described coatings 24 may be applied to core 22 by numerous means well-known in the art. For example, coatings 24 may be applied by the following methods: anodizing, dying, electro-coating, photoluminescent coating, application of nitrides, methyl methacrylate, painting, powder coating, coating with paraffins, oil stains or phosphor coatings, the use of hydroxyapatite, polymers, titanium oxinitrides, zinc sulfides, carbides, etc. It should be noted that, while the listed coatings 24 are fairly specific as disclosed herein, other coatings known in the art to enhance visibility of core 22 are within the contemplated scope of the present disclosure.

During the specific coating of core 22 with coatings 24, tissue penetrating tips 18 and 20 may be masked, or otherwise covered to avoid receiving coating 24. This may be desirable to prevent blunting of tissue penetrating tips 18 and 20 thereby enabling tips 18 and 20 to more cleanly penetrate tissue.

Figure 2:
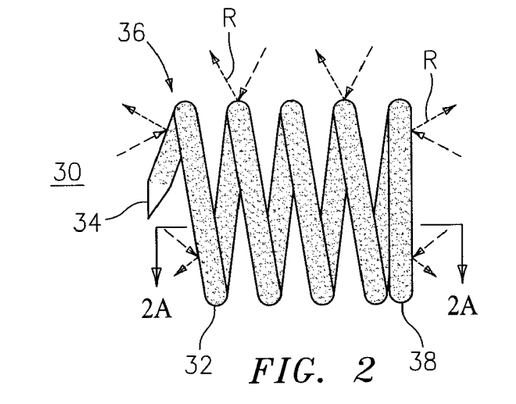
FIG. 2 is a side view of an alternative embodiment of a coated surgical staple.
Figure 2A:
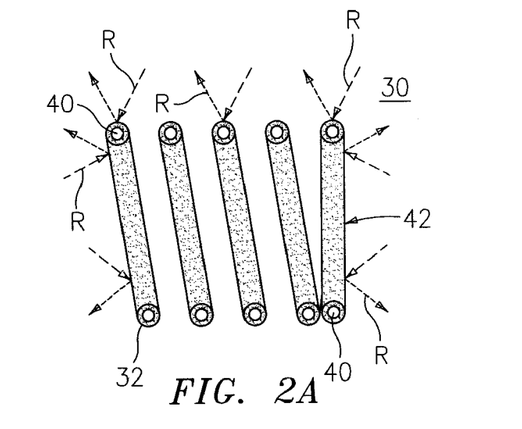
FIG. 2A is a side view, partially shown in section, of the coated surgical staple of FIG. 2.

Referring now to FIGS. 2 and 2A, and initially with respect to FIG. 2, there is disclosed an alternative fastener or coil fastener 30 also configured to be easily visualized within tissue without the aid of reflected light. Coil fastener 30 generally includes a helical coil body 32 having a tissue penetrating tip 34 formed on a distal end 36 of helical coil body 32. Helical coil body 32 additionally includes a compressed proximal end coil 38 to facilitate driving coil fastener 30 into tissue.

Referring specifically to FIG. 2A, and like staple 10 described hereinabove, coil fastener 30 includes a metal core 40 having an active coating 42 applied thereto. Coating 42 also emits visible rays "R" which enable coil faster 30 to be easily visualized within tissue. Coating 42 is formed from, and is applied to core 40, in manners similar to that described hereinabove with respect to staple 10. As with tissue penetrating tips 18 and 20 described hereinabove with respect to staple 10, tissue penetrating tip 34 may be covered during coating to avoid blunting.

Figure 3:
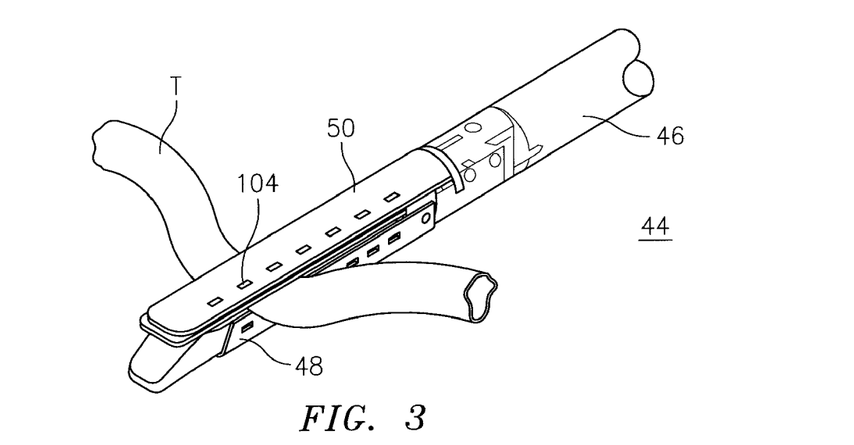
FIG. 3 is a perspective view of the distal end of a surgical stapling device positioned about a tubular tissue section.
Figure 4:
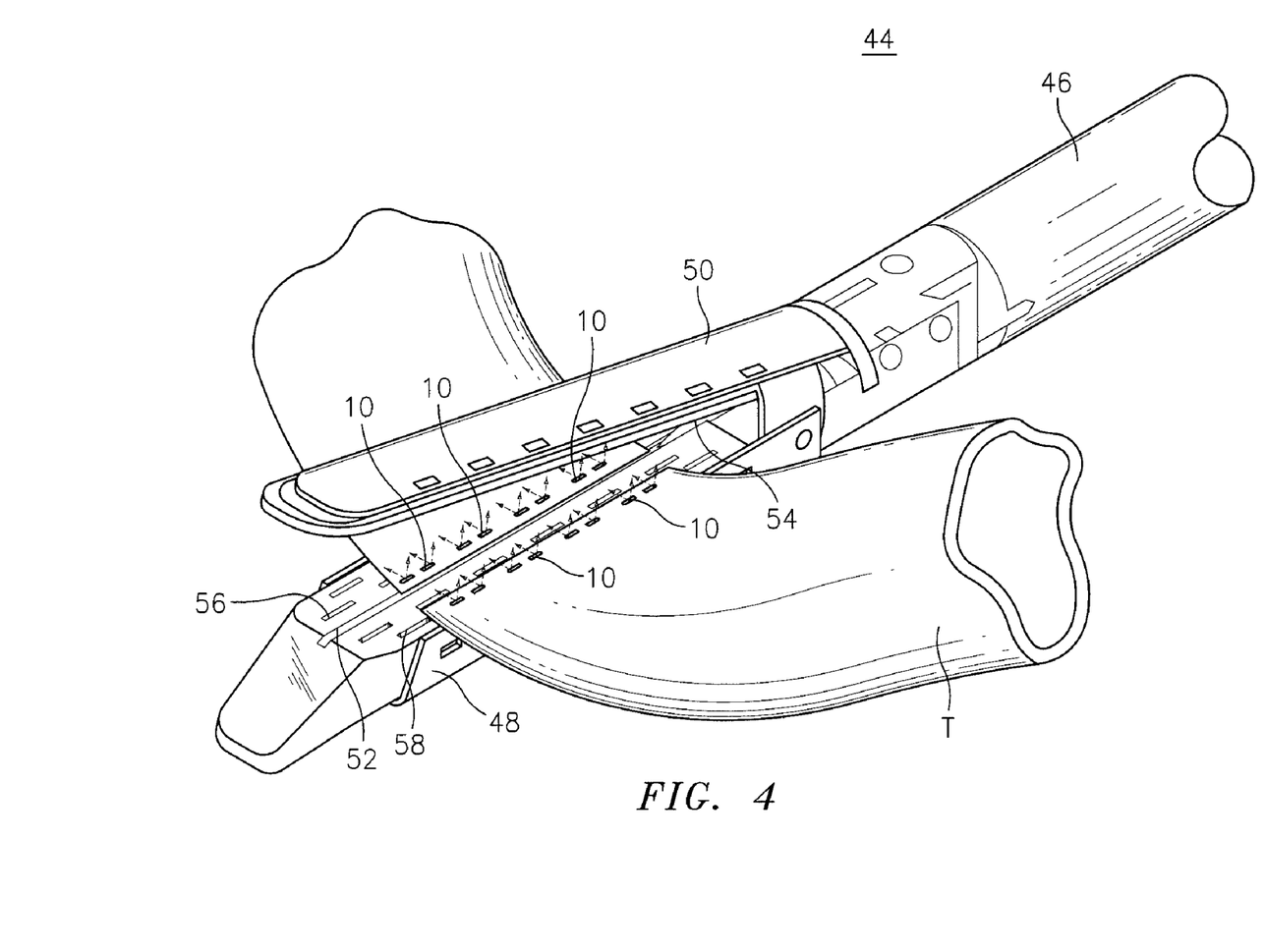
FIG. 4 is a perspective view of the distal end of the surgical stapling device and tubular tissue section of FIG. 3 after stapling and cutting the tubular tissue section.

Referring now to FIGS. 3 and 4, and initially with respect to FIG. 3, the use of a surgical stapling device (not shown) having a distal end 44 portion to apply a fastener, such as, for example, staple 10 to tissue will now be described. Distal end 44 portion includes an elongate tubular member 46 having a staple cartridge 48 mounted thereto. An anvil member 50 is movably attached to elongate tubular member 46 and is movable between an open position substantially spaced apart from staple cartridge 48 to a closed position substantially adjacent staple cartridge 48.

Referring to FIG. 4, staple cartridge 48 is formed with a knife slot 52 extending longitudinally through staple cartridge 48. A knife blade 54 is associated with distal end 44 and movable through knife slot 52 so as to sever tissue captured between staple cartridge 48 and anvil member 50. Staple cartridge 48 further includes multiple rows of staples 10 positioned within staple pockets 56 for application to a tissue, such as tubular tissue section T. In use, distal end 44 is applied to tissue section T such that tissue section T is captured between staple cartridge 48 and anvil member 50 movably mounted on elongate tubular member 46. Thereafter, the surgical stapler is actuated so as to eject staples 10 from staple pockets 56 within staple cartridge 48, through tissue section T and into anvil member 50 thereby stapling tissue section T in a known manner. Thereafter, knife blade 54 is advanced through knife slot 52 so as to cut tubular tissue section T between rows of staples 10 now applied to tubular tissue section T.

Upon removal of distal end 44 of the surgical stapler from about tubular tissue section T, the rows of staples 10, as well as the proper formation of each individual staple 10, can be easily visualized in the now free ends of tubular tissue section T by rays "R" emitted from staples 10. Thus, the proper positioning and formation of staples 10 within a tissue section can be easily visualized without being obscured by reflected light.

Figure 5:
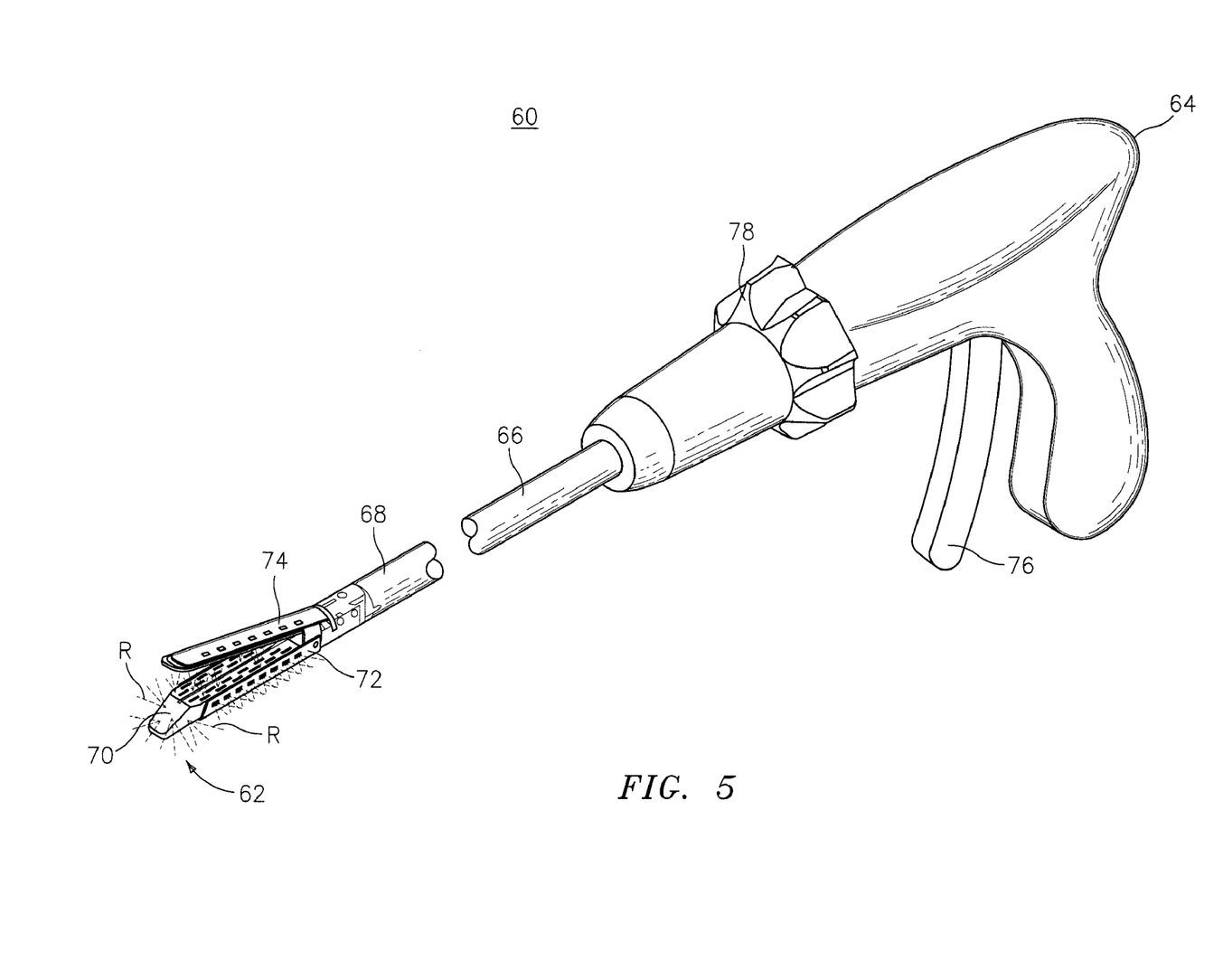
FIG. 5 is a perspective view of a surgical stapling device incorporating a staple cartridge to illuminate the distal end of the surgical stapling device.

Referring now to FIG. 5, there is disclosed a surgical stapler 60 having staple cartridge 62 incorporating one or more light sources to facilitate visualizing the positioning of staple cartridge 62 within the body of a patient. Additionally, as described in more detail hereinbelow, staple cartridge 62 also provides an indication of proper functioning of surgical stapler 60 as it applies staples to tissue and cuts the staple tissue. Surgical stapler 60 generally includes a pistol grip handle 64 having an elongated tubular member 66 extending distally from pistol grip handle 64. Illuminated staple cartridge 62 is mounted on a distal end 68 of elongate tubular member 66 and includes a transparent cartridge insert 70 housed within a generally U-shaped outer channel 72. Cartridge insert 70 is provided to transmit optical radiation, in the form of a visible light, to the area surrounding illuminated staple cartridge 62 while U-shaped outer channel 72 shields a portion of the optical radiation. One or more light sources may be associated with surgical stapler 60 to provide a light source for illuminating staple cartridge 62.

An anvil member 74 is movably mounted to distal end 68 of elongated tubular member 66. Anvil member 74 is movable from an open position spaced apart from illuminated staple cartridge 62 to a closed position substantially adjacent to illuminated staple cartridge 62. A trigger 76 is provided on pistol grip handle 64 to move anvil member 74 between the open and closed positions, as well as, to eject staples from illuminated staple cartridge 62 in a manner described in more detail hereinbelow. Finally, a rotation collar 78 is provided to rotate elongate tubular member 66 and orient illuminated staple cartridge 62 and anvil member 74 relative to tissue.

Figure 6:
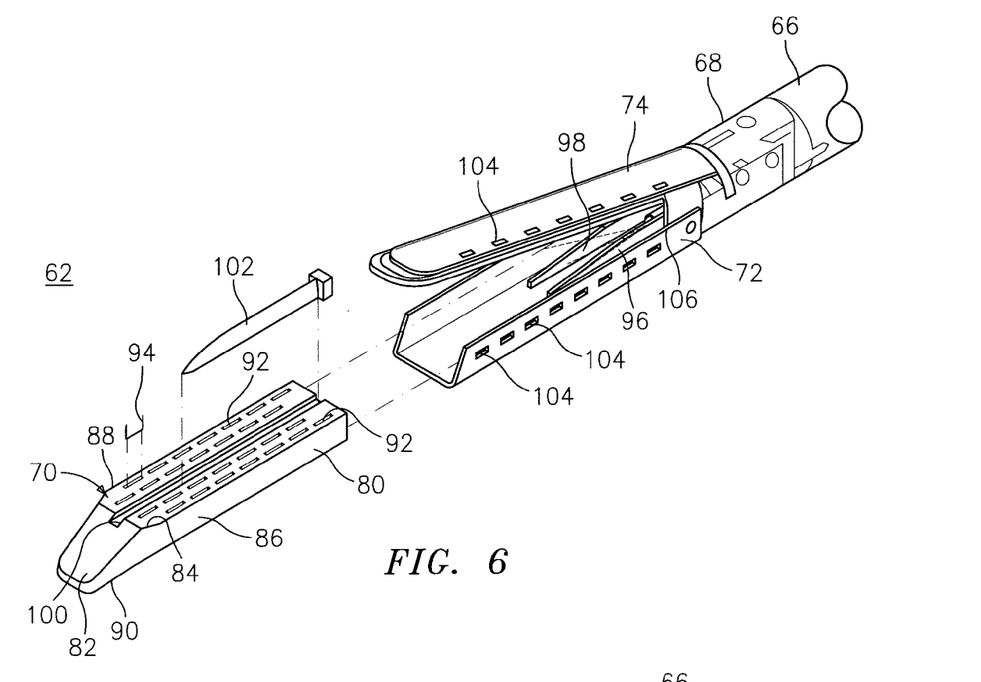
FIG. 6 is a perspective view, with parts separated, of the distal end of the surgical stapling device.

Referring now to FIG. 6, cartridge insert 70 generally includes a body portion 80 having a tapered leading edge 82. As noted hereinabove, body portion 80 is transparent to optical radiation such that once a light source is applied to body portion 80, light rays are emitted from a face surface 84, side surfaces 86 and 88, as well as from an undersurface 90 of body portion 80.

Body portion 80 additionally includes a plurality of staple pockets 92 containing staples 94 for insertion into tissue. Staples 94 may be conventional in manner or may be similar to those described with respect to staple 10 hereinabove. Staple drivers 96 and 98 are provided to extend into corresponding slots in cartridge insert 70 and drive staples 94 out of staple pockets 92 and into tissue. A knife slot 100 extends longitudinally through body portion 80 and face surface 84. A knife blade 102 is associated with surgical stapler 60 and is movable through knife slot 100 so as to sever tissue captured between illuminated staple cartridge 62 and anvil member 74.

As shown, U-shaped outer channel member 72 includes a plurality of windows 104. Windows 104 are provided for the passage of light rays from side surfaces 86 and 88 of body portion 80. Windows 104 may additionally be used as mounting structures for corresponding projections formed in body portion 80 (not shown) to facilitate mounting cartridge insert 70 within U-shaped outer channel 72.

As noted hereinabove, surgical stapler 60 may be provided with various light sources to facilitate illumination of and through insert 70. In one embodiment, surgical stapler 60 is provided with a light source 106 positioned within distal end 68 of elongate tubular member 66. Light source 106 may include one or more lights including LED lights, incandescent lights, electroluminescent lights, light sources utilizing xenon or halogen bulbs, etc. or may be channeled to its desired location by fiber optic filaments or wire, while light source 106 is disclosed as being positioned within distal end 68 of elongate tubular member 66, light source 106 may alternatively be incorporated directly into cartridge insert 70. In an alternative embodiment, light source 106 may be an additive infused in cartridge insert 70 having a UV reactive light fluorescence or phosphorescent additive to allow cartridge 70 to be visible. Furthermore, additional means may be utilized to channel a light source via a fiber-optic conduit to cartridge insert 70. Surfaces of cartridge insert 70 may be polished or coated with a reflective material to amplify and focus the light source forward towards tapered leading edge 82 of body portion 80.

While not specifically shown, surgical stapler 60, and in particular, handle 64 may be provided with various known means of supplying light, and/or electricity, to staple cartridge 62. Various known means of providing electricity along with switching mechanisms are well-known in the art with respect to electrocaurtery devices and may be incorporated into handle 64.

Figure 7:
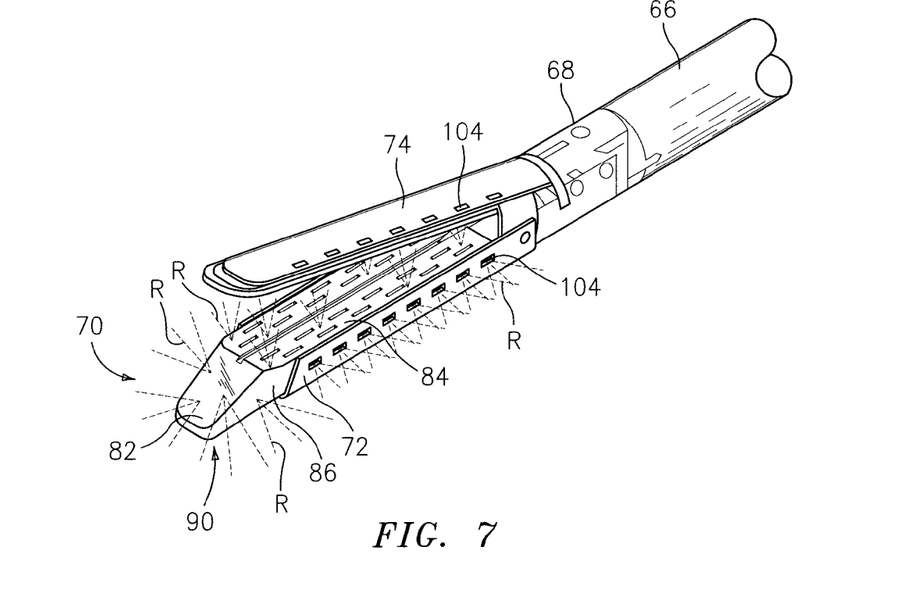
FIG. 7 is a perspective view of the assembled and illuminated distal end of the surgical stapling device.

Referring now to FIG. 7, and as noted hereinabove, illumination of cartridge insert 70 causes light rays "R" to be emitted from body portion 80. Specifically, as shown, light rays "R" are emitted from tapered leading edge 82 and face surface 84 so as to allow proper positioning of illuminated staple cartridge 62 within the body of a patient. Further, as body portion 80 projects distally beyond U-shaped outer channel 72, light rays emanating from undersurface 90 can be used to determine the specific orientation of anvil member 74 and illuminated staple cartridge 62 within the body of a patient. Additionally, light rays "R" emitted from side surfaces 86 and 88 project through windows 104 formed in U-shaped outer channel 72. The intensity of the light rays "R" emitted through windows 104 may be also utilized to give a general indication of the positioning of staple drivers 96 and 98 as well as the position of knife blade 102 within body portion 80 of cartridge insert 70 and/or the anvil member 74.

Figures 8, 9:
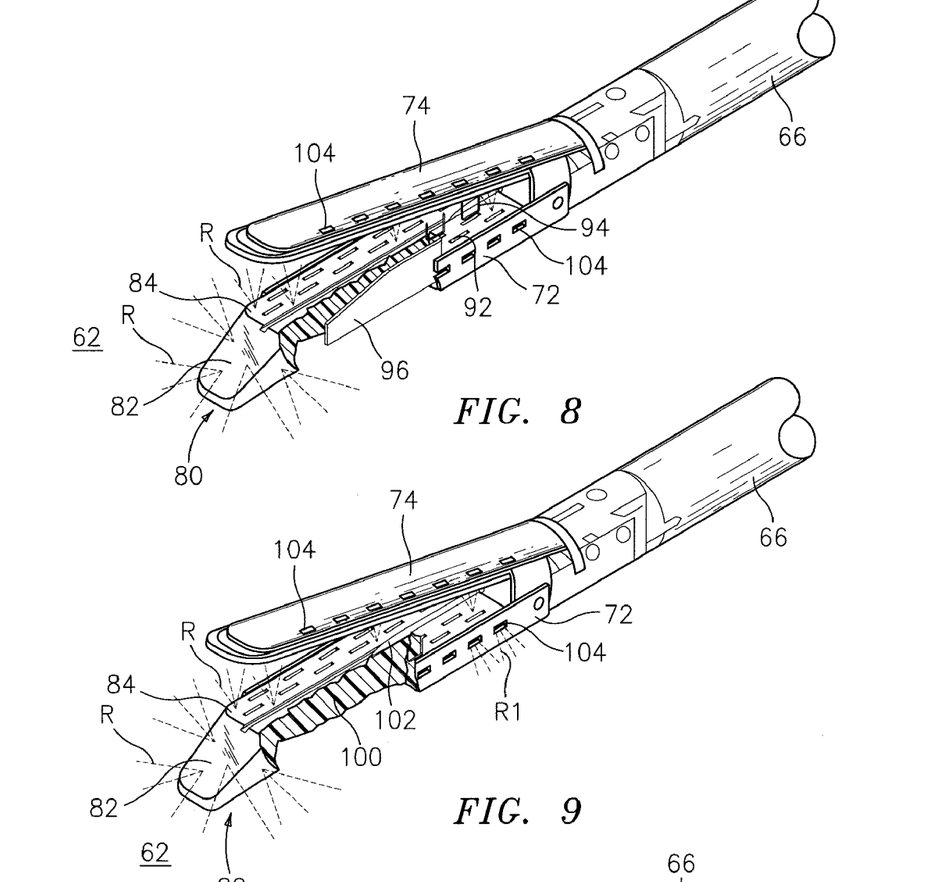
FIG. 8 is a perspective view of the distal end of the surgical stapling device, with an anvil in the open position, partially illuminated during a stapling stroke.
FIG. 9 is a perspective view of the distal end of the surgical stapling device, with the anvil in the open position, partially illuminated during a cutting stroke.

Referring now to FIGS. 8 and 9, movement of staple drivers 96 and 98 as well as movement of knife blade 102 within body portion 80 of cartridge insert 70 blocks internal transmission of a portion of the light provided to cartridge insert 70 by light source 106. With specific reference to FIG. 8, as staple driver 96 moves distally within body portion 80 to eject staples 94 out of staple pockets 92, staple driver 96 blocks the substantial amount of light internal to body portion 80 thereby greatly diminishing or eliminating the amount of light projected from windows 104 in U-shaped outer channel 72. During use, the surgeon may take advantage of this feature by noting how many windows 104 adjacent the proximal end of illuminated staple cartridge 62 are not emitting light thereby giving an indication of the position of staple driver 96 and thus an indication of which staples 94 have been actually fired into tissue.

As shown in FIG. 9, as knife blade 102 is advanced within knife slot 100 formed within body portion 80 a specific amount of light from one side of body portion 80 is prevented from being transmitted to the opposed side of body portion 80 by the presence of knife blade 102. This results in a reduced or diminished amount of light rays "R1" projecting out of windows 104 in U-shaped outer channel 72. Thus, the position of knife blade 104 within illuminated staple cartridge 62 can be determined during use by the surgeon to assure that a subject tissue section has been completely cut.

Figure 10:
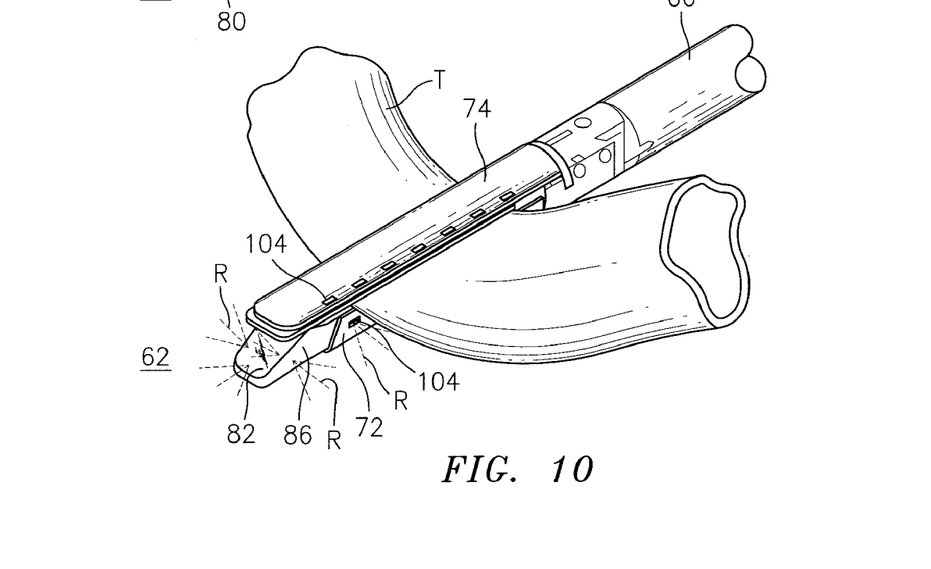
FIG. 10 is a perspective view of the partially illuminated distal end of the surgical stapling device positioned about a tubular tissue section.

Referring now to FIG. 10, in situations where the subject tissue section, such as, for example tissue section T is obscured, i.e., is not completely visible to the surgeon, illuminated staple cartridge 62 may be used in a manner to identify the location of tissue section T and/or assure that tissue section T has been properly grasped between illuminated staple cartridge 62 and anvil member 74. For example, as shown, when viewed slightly from above, tissue section T obscures light rays emitted from most of windows 104 while allowing light rays to be visible off of tapered leading edge 82 and a distal most window 104.

Thus, in this manner it can be seen that staple cartridge 62 can be utilized to both indicate the positioning of the distal end of the surgical stapler within the body of a patient as well as given indication of the relative positions of the staple drivers and knife blade within staple cartridge 62 itself.

It will be understood that various modifications may be made to the embodiments disclosed herein. For example, the above disclosure may relate to fasteners other than the disclosed conventional staple and helical coil fasteners such as, for example, surgical clips, two-part fasteners, etc. Further, while the above disclosure is given with regard to illuminating a staple cartridge and a surgical stapling device, the present disclosure may find equal utility when incorporated into a surgical instrument having a pair of jaws by illuminating one or both of the jaws to facilitate visualization of the orientation of the surgical instrument within a patient. Additionally, and as noted hereinabove, the disclosed insert within the illuminated staple cartridge and/or anvil may be completely transparent or may include specific zones or regions of transparency so as to facilitate visualization by an operator. Therefore, the above description should not be construed as limiting, but merely as exemplifications of particular embodiments. Those skilled in the art will envision other modifications within the scope and spirit of the claims appended hereto.

The invention claimed is:

1. A surgical fastener comprising:
   a core material having at least one tissue penetrating tip; and
   a non-reflective coating applied to at least a portion of the core material, the non-reflective coating emitting visible rays.

2. The surgical fastener as recited in claim 1, wherein the non-reflective coating has a molecular fluorescence.

3. The surgical fastener as recited in claim 1, wherein the non-reflective coating has a molecular phosphorescence.

4. The surgical fastener as recited in claim 1, wherein the non-reflective coating is chemiluminescent.

5. The surgical fastener as recited in claim 1, wherein the at least one tissue penetrating tip of the fastener is uncoated.

6. The surgical fastener as recited in claim 1, wherein the core material is formed into a backspan and a leg extending from each end of the backspan.

7. The surgical fastener as recited in claim 6, wherein each leg extending from the backspan terminates in the tissue penetrating tip.

8. The surgical fastener as recited in claim 1, wherein the core material is formed into a helical coil terminating in a tissue penetrating tip at one end and a compressed coil at an opposing end.

9. A surgical stapling device comprising;
   a handle;
   an elongate tubular member extending distally from the handle;
   an illuminated staple containing cartridge mounted on a distal end of the elongate tubular member; and
   a light source associated with the distal end of the elongate tubular member, such that light emitted from the light source is transmitted to the illuminated staple containing cartridge, wherein the transmitted light is emitted by the illuminated staple containing cartridge.

10. The surgical stapling device as recited in claim 9, wherein the illuminated staple containing cartridge includes a U-shaped outer channel and a transparent staple containing insert.

11. The surgical stapling device as recited in claim 10, wherein a portion of the transmitted light passes through the transparent staple containing insert.

12. The surgical stapling device as recited in claim 9, wherein the U-shaped outer channel includes a plurality of windows.

13. The surgical stapling device as recited in claim 12, wherein a portion of the transmitted light passes through the plurality of windows.

* * * * *